United States Patent
Hoey et al.

(10) Patent No.: US 6,494,902 B2
(45) Date of Patent: *Dec. 17, 2002

(54) METHOD FOR CREATING A VIRTUAL ELECTRODE FOR THE ABLATION OF TISSUE AND FOR SELECTED PROTECTION OF TISSUE DURING AN ABLATION

(75) Inventors: Michael F. Hoey, Shoreview, MN (US); Peter M. J. Mulier, Stillwater, MN (US)

(73) Assignee: Medtronic, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/347,363

(22) Filed: Jul. 6, 1999

(65) Prior Publication Data
US 2002/0058935 A1 May 16, 2002

Related U.S. Application Data

(60) Provisional application No. 60/091,937, filed on Jul. 7, 1998.

(51) Int. Cl.[7] .................................................. A61F 7/00
(52) U.S. Cl. .......................... 607/105; 606/41; 128/898
(58) Field of Search ............................. 606/41, 45–50; 607/101–105; 604/22; 128/898

(56) References Cited

U.S. PATENT DOCUMENTS

| | | | |
|---|---|---|---|
| 5,403,311 A | * | 4/1995 | Abele et al. .................. 606/50 |
| 5,431,649 A | * | 7/1995 | Mulier et al. .................. 606/41 |
| 5,433,708 A | | 7/1995 | Nichols et al. |
| 5,472,441 A | * | 12/1995 | Edwards et al. ............... 606/41 |
| 5,542,928 A | | 8/1996 | Evans et al. |
| 5,584,872 A | | 12/1996 | LaFontaine et al. |
| 5,599,346 A | * | 2/1997 | Edwards et al. ............... 606/41 |
| 5,609,151 A | | 3/1997 | Mulier |
| 5,653,692 A | | 8/1997 | Masterson et al. |

(List continued on next page.)

*Primary Examiner*—Michael Peffley
(74) *Attorney, Agent, or Firm*—Daniel W. Latham, Esq.; Timothy A. Czaja

(57) ABSTRACT

The present invention provides an apparatus and a method for producing a virtual electrode within or upon a tissue to be treated with radiofrequency alternating electric current, such tissue including but not limited to liver, lung, cardiac, prostate, breast, and vascular tissue and neoplasms. An apparatus in accordance with the present invention includes a radiofrequency alternating electric current source and a radiofrequency ablating a fluid source. A surgical instrument is connected to both the current source and the fluid source for delivering a fluid and a current to a first portion of tissue to be ablated. The apparatus also includes a protective fluid source and a delivery system connected to the protective fluid source for delivery of protective fluid to a secondary portion of tissue whose ablation is not desired.

A method in accordance with the present invention will include the steps of providing a radiofrequency ablating fluid to a first portion of tissue to be ablated, providing a radiofrequency alternating electric current to the first portion of tissue to be ablated, and providing a protective fluid to a second portion of tissue whose ablation is not desired.

26 Claims, 2 Drawing Sheets

U.S. PATENT DOCUMENTS

| | | |
|---|---|---|
| 5,676,693 A | 10/1997 | LaFontaine |
| 5,697,281 A | 12/1997 | Eggers et al. |
| 5,697,536 A | 12/1997 | Eggers et al. |
| 5,697,909 A | 12/1997 | Eggers et al. |
| 5,697,927 A | 12/1997 | Imran et al. |
| 5,725,524 A | 3/1998 | Mulier et al. |
| 5,800,482 A | 9/1998 | Pomeranz et al. |
| 5,807,395 A | 9/1998 | Mulier et al. |
| 5,861,021 A * | 1/1999 | Thome et al. .............. 607/101 |
| 5,876,398 A | 3/1999 | Mulier et al. |
| 5,888,198 A | 3/1999 | Eggers et al. |
| 5,891,095 A | 4/1999 | Eggers et al. |
| 5,895,417 A | 4/1999 | Pomeranz et al. |
| 5,897,553 A | 4/1999 | Mulier et al. |
| 5,902,328 A | 5/1999 | LaFontaine et al. |
| 5,906,613 A | 5/1999 | Mulier et al. |
| 5,913,854 A | 6/1999 | Maguire et al. |
| 6,004,319 A * | 12/1999 | Goble et al. ................... 606/48 |
| 6,081,749 A * | 6/2000 | Ingle et al. .................. 607/101 |
| 6,238,393 B1 * | 5/2001 | Mulier et al. ................. 606/41 |
| 2001/0025178 A1 * | 9/2001 | Mulier et al. ................. 606/41 |

* cited by examiner

METHOD FOR CREATING A VIRTUAL ELECTRODE FOR THE ABLATION OF TISSUE AND FOR SELECTED PROTECTION OF TISSUE DURING AN ABLATION

This application is based upon and claims the benefit of U.S. Provisional Application No. 60/091,937, filed on Jul. 7, 1998.

FIELD OF THE INVENTION

The present invention relates generally to an apparatus and method for creating a virtual electrode. More particularly, the present invention relates to an apparatus and method for the creation of a virtual electrode that is useful for the ablation of soft tissue and neoplasms.

BACKGROUND OF THE PRESENT INVENTION

The utilization of an electric current to produce an ameliorative effect on a bodily tissue has a long history, reportedly extending back to the ancient Greeks. The effects on bodily tissue from an applied electric current, and thus the dividing line between harmful and curative effects, will vary depending upon several factors, including voltage levels, current levels, the length of time the current is applied, and the tissue involved. One such effect resulting from the passage of an electric current through tissue is heat generation.

Body tissue, like all non-superconducting materials, conducts current with some degree of resistance. This resistance creates localized heating of the tissue through which the current is being conducted. The amount of heat generated will vary with the power P deposited in the tissue, which is a function of the product of the square of the current I and the resistance R of the tissue to the passage of the current through it ($P=I^2R$.).

As current is applied to specific tissue, heat is generated in that tissue due to the inherent resistance of the tissue. Deleterious effects in the cells making up the tissue begin to occur at about 42° Celsius, depending on the length of time that the cells are exposed to the generated heat. As the temperature of the tissue increases due to the heat generated by the tissue's resistance, the tissue will undergo profound changes and eventually, as the temperature becomes high enough, that is, generally greater than 45° C., the cells will die. The zone of cell death is known as a lesion and the procedure followed to create the lesion is commonly called an ablation. As the temperature increases beyond cell death temperature, complete disintegration of the cell walls and cells caused by boiling off of the water within the tissue can occur. Cell death temperatures can vary somewhat with the type of tissue to which the power is being applied, but generally will begin to occur within the range of 45° to 60° C., though actual cell death of certain tissue cells may occur at a higher temperature.

In recent times, electric current has found advantageous use in surgery, with the development of a variety of surgical instruments for cutting tissue or for coagulating blood. Still more recently, the use of alternating electric current to ablate, that is, kill, various tissues has been explored. Typically, current having a frequency from about 3 kilohertz to about 300 gigahertz, which is generally known as radiofrequency (RF) current, is used for this procedure. Destruction of tissue using an RF current is commonly known as RF ablation. Often RF ablation is performed as a minimally invasive procedure and is known as RF catheter ablation because the procedure is performed through and with the use of a catheter. By way of example, RF catheter ablation has been used to ablate cardiac tissue responsible for irregular heartbeat arrhythmias.

The prior art applications of providing current to specific tissue have typically involved applying the current using a "dry" electrode. That is, a metal electrode is applied to the tissue desired to be affected and a generated electric current is passed through the electrode to the tissue. A commonly known example of an instrument having such an operating characteristic is an electrosurgical instrument known as a "bovie" knife. This instrument includes a cutting/coagulating blade electrically attached to a current generator. The blade is applied to the tissue of a patient and the current passes through the blade into the tissue and through the patient's body to a metal base electrode or ground plate usually placed underneath and in electrical contact with the patient. The base electrode is in turn electrically connected to the current generator so as to provide a complete circuit.

As the current from the bovie knife passes from the blade into the tissue of a patient, the resistance provided by the tissue creates heat. In the cutting mode, a sufficient application of power through the bovie knife to the tissue causes the fluid within the cell to turn to steam, creating a sufficient overpressure so as to burst the cell walls. The cells then dry up, desiccate, and carbonize, resulting in localized shrinking and an opening in the tissue. Alternatively, the bovie knife can be applied to bleeding vessels to heat and coagulate the blood flowing therefrom and thus stop the bleeding.

As previously noted, another use for electrical instruments in the treatment of the body is in the ablation of tissue. To expand further on the brief description given earlier of the ablation of cardiac tissue, it has long been known that a certain kind of heart tissue known as sino-atrial and atrio-ventricular nodes spontaneously generate an electrical signal that is propagated throughout the heart along conductive pathways to cause it to beat. Occasionally, certain heart tissue will "misfire," causing the heart to beat irregularly. If the errant electrical pathways can be determined, the tissue pathways can be ablated and the irregular heartbeat remedied. In such a procedure, an electrode is placed via a catheter into contact with the tissue and then current is applied to the tissue via the electrode from a generator of RF current. The applied current will cause the tissue in contact with the electrode to heat. Power will continue to be applied until the tissue reaches a temperature where the heart tissue dies, thereby destroying the errant electrical pathway and the cause of the irregular heartbeat.

Another procedure using RF ablation is transurethral needle ablation, or TUNA, which is used to create a lesion in the prostate gland for the treatment of benign prostatic hypertrophy (BPH) or the enlargement of the prostate gland. In a TUNA procedure, a needle having an exposed conductive tip is inserted into the prostate gland and current is applied to the prostate gland via the needle. As noted previously, the tissue of the prostate gland heats locally surrounding the needle tip as the current passes from the needle to the base electrode. A lesion is created as the tissue heats and the destroyed cells may be reabsorbed by the body, infiltrated with scar tissue, or just become non-functional.

While there are advantages and uses for such "dry" electrode instruments, there are also several notable disadvantages. One of these disadvantages is that during a procedure, coagulum—dried blood cells and tissue cells—will form on the electrode engaging the tissue. Coagulum acts as an insulator and effectively functions to prevent current transfer from the blade to the tissue. This coagulum "insulation" can be overcome with more voltage so as to keep the current flowing, but only at the risk of arcing and injuring the patient. Thus, during surgery when the tissue is cut with an electrosurgical scalpel, a build-up of coagulated blood and desiccated tissue will occur on the blade, requiring the blade to be cleaned before further use. Typically, cleaning an electrode/scalpel used in this manner will involve simply scraping the dried tissue from the electrode/scalpel by rubbing the scalpel across an abrasive pad to remove the coagulum. This is a tedious procedure for the surgeon and the operating staff since it requires the "real" work of the surgery to be discontinued while the cleaning operation occurs. This procedure can be avoided with the use of specially coated blades that resist the build up of coagulum. However, such specialty blades are costly.

A second disadvantage of the dry electrode approach is that the electrical heating of the tissue creates smoke that is now known to include cancer-causing agents. Thus, preferred uses of such equipment will include appropriate ventilation systems, which can themselves become elaborate and expensive.

A further, and perhaps the most significant, disadvantage of dry electrode electrosurgical tools is revealed during cardiac ablation procedures. During such a procedure, an electrode that is otherwise insulated but having an exposed, current carrying tip is inserted into the heart chamber and brought into contact with the inner or endocardial side of the heart wall where the ablation is to occur. The current is initiated and passes from the current generator to the needle tip electrode and from there into the tissue so that a lesion is created. Typically, however, the lesion created by a single insertion is insufficient to cure the irregular heartbeat because the lesion created is of an insufficient size to destroy the errant electrical pathway. Thus, multiple needle insertions and multiple current applications are almost always required to ablate the errant cardiac pathway, prolonging the surgery and thus increasing the potential risk to the patient.

This foregoing problem is also present in TUNA procedures, which similarly require multiple insertions of the needle electrode into the prostate gland. Failing to do so will result in the failure to create a lesion of sufficient size required for beneficial results. As with RF catheter ablation of cardiac tissue, the ability to create a lesion of the necessary size to alleviate BPH symptoms is limited and thus requires multiple insertions of the electrode into the prostate.

A typical lesion created with a dry electrode using RF current and a single insertion will normally not exceed one centimeter in diameter. This small size—often too small to be of much or any therapeutic benefit—stems from the fact that the tissue surrounding the needle electrode tends to desiccate as the temperature of the tissue increases, leading to the creation of a high resistance to the further passage of current from the needle electrode into the tissue. This high resistance—more properly termed impedance since typically an alternating current is being used—between the needle electrode and the base electrode is commonly measured by the RF current generator. When the measured impedance reaches a pre-determined level, the generator will discontinue current generation. Discontinuance of the ablation procedure under these circumstances is necessary to avoid injury to the patient.

Thus, a typical procedure with a dry electrode may involve placing the needle electrode at a first desired location; energizing the electrode to ablate the tissue; continue applying current until the generator measures a high impedance and shuts down; moving the needle to a new location closely adjacent to the first location; and applying current again to the tissue through the needle electrode. This expanded cycle of electrode placement, electrode energization, generator shut down, electrode re-emplacement, and electrode re-energization, will be continued until a lesion of the desired size has been created, thereby increasing the length of the procedure for the patient. Additionally, multiple insertions increases the risk of at least one of the placements being in the wrong location and, consequently, the risk that healthy tissue may be undesirably affected while diseased tissue may be left untreated. The traditional RF ablation procedure of using a dry ablation therefore includes several patient risk factors that both patient and physician would prefer to reduce or eliminate.

The therapeutic advantages of RF current could be increased if a larger lesion could be created safely with a single positioning of the current-supplying electrode. A single positioning would allow the procedure to be carried out both more expeditiously and more efficiently, reducing the time involved in the procedure. Prior art therapies creating larger lesions simply continue to apply current to the patient with sufficiently increasing power to overcome the previously discussed coagulum insulation issue, thereby creating a larger lesion. However, the patient is subject to undesirable results, such as painful damage to healthy tissue.

It would be desirable to have an apparatus capable of creating a virtual electrode for the controlled application of tissue ablating RF electric current to a tissue of interest so as to produce a lesion of desired size and configuration.

SUMMARY OF THE INVENTION

It is an object of the present invention to provide a new and improved apparatus and method that is not subject to the foregoing disadvantages.

It is another object of the present invention to provide an integrated conductive fluid supply and radiofrequency current generator.

It is a further object of the present invention to provide an apparatus and method for treating a patient with radiofrequency current via a virtual electrode to produce a lesion of a predetermined size.

It is a further object of the present invention to provide an apparatus and method which protects a portion of tissue whose ablation is not desired.

The foregoing objects of the present invention are achieved by an apparatus and a method for producing a virtual electrode within or upon a tissue to be treated with radiofrequency alternating electric current, such tissue including but not limited to liver, lung, cardiac, prostate, breast, and vascular tissue and neoplasms. An apparatus in accordance with the present invention will include a surgical instrument connected to a radiofrequency alternating electric current source and connected to a radiofrequency ablating fluid source. The surgical instrument delivers a fluid and a current to a first portion of tissue to be ablated. The apparatus also includes a delivery instrument connected to a protective fluid source for delivery of a protective fluid to a second portion of tissue whose ablation is not desired.

A method of creating a virtual electrode for the ablation of tissue and for the selected protection of tissue during an ablation therapy includes providing a radiofrequency ablation fluid to a first portion of tissue to be ablated, providing a radiofrequency alternating electric current to the first portion of tissue to be ablated, and providing a protection fluid to a second portion of tissue whose ablation is not desired.

The foregoing objects of the invention will become apparent to those skilled in the art when the following detailed description of the invention is read in conjunction with the accompanying drawings and claims. Throughout the drawings, like numerals refer to similar or identical parts.

DESCRIPTION OF THE PREFERRED EMBODIMENTS

Research conducted under the auspices of the assignee of the present invention has focused on spreading the current density throughout a larger tissue volume through the creation, maintenance, and control of a "virtual electrode" within or adjacent to the tissue to be ablated. A virtual electrode can be created by the introduction of a conductive fluid, such as isotonic or hypertonic saline, into or onto the tissue to be ablated. The conductive fluid will facilitate the spread of the current density substantially equally throughout the extent of the flow of the conductive fluid, thus creating an electrode—a virtual electrode—substantially equal in extent to the size of the delivered conductive fluid. Radiofrequency (RF) current can then be passed through the virtual electrode into the tissue.

A virtual electrode can be substantially larger in volume than the needle tip electrode typically used in prior art RF interstitial ablation procedures and thus can create a larger lesion than can a dry, needle tip electrode. That is, the virtual electrode spreads or conducts the RF current density outward from the RF current source—such as a current carrying needle, forceps, or other current delivery device—into or onto a larger volume of tissue than is possible with instruments that rely on the use of a dry electrode. Stated otherwise, the creation of the virtual electrode enables the current to flow with reduced resistance or impedance throughout a larger volume of tissue, thus spreading the resistive heating created by the current flow through a larger volume of tissue and thereby creating a larger lesion than could otherwise be created with a dry electrode.

Figure 1:
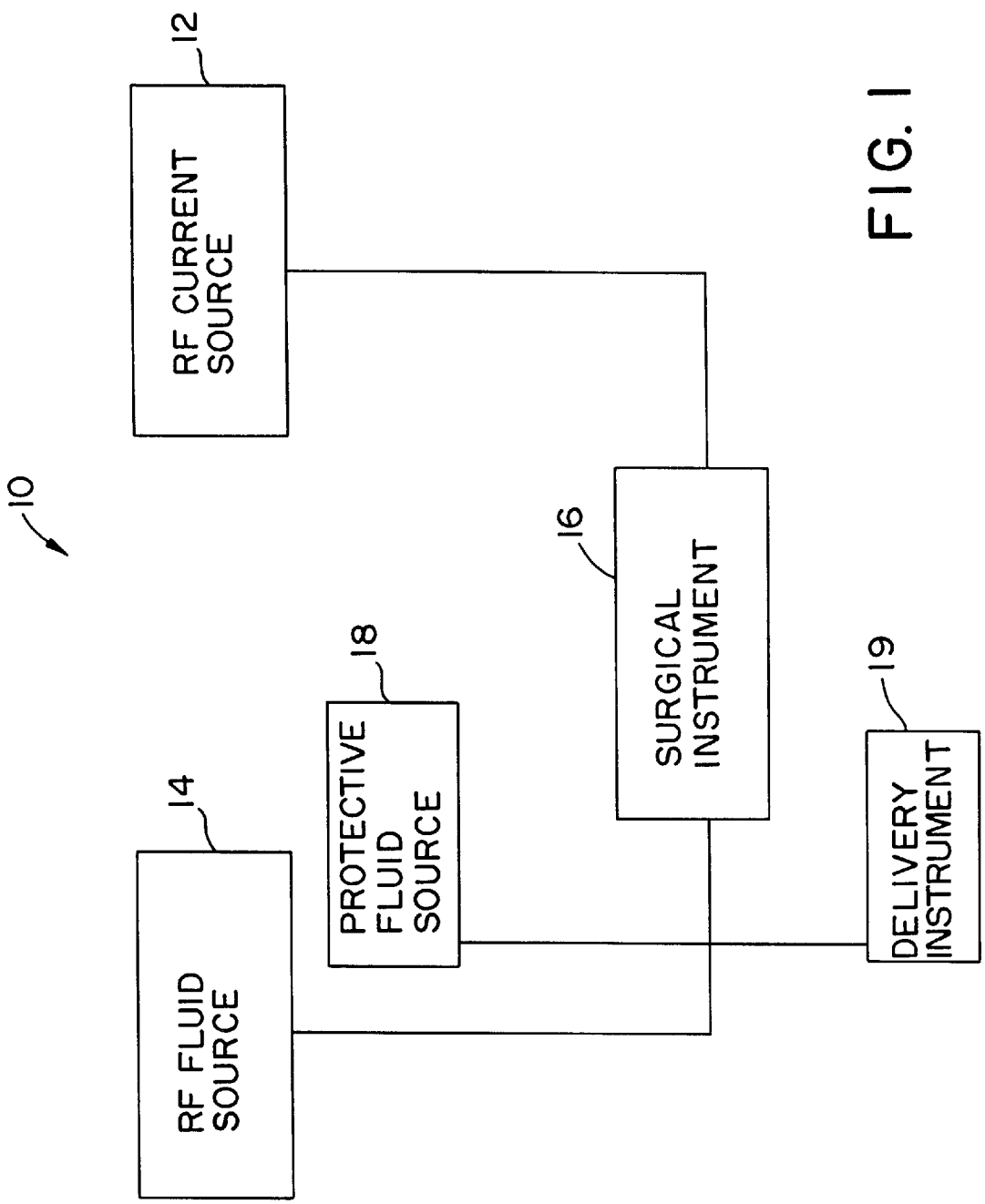
FIG. 1 is a schematic representation showing a radiofrequency ablation system incorporating the present invention.

FIG. 1 illustrates in schematic form a system for RF ablation useful with the present invention. System 10 includes a source of radiofrequency alternating electric current 12, a source of RF ablating fluid 14, including but not limited to saline and other conductive solutions, and surgical instrument 16 for delivering the RF current and the RF ablation fluid to a desirous tissue site for ablation purposes. For this application, RF current is defined as current having a frequency from about 3 kilohertz to 300 gigahertz. It is understood that surgical instrument 16 may be a single needle within a RF ablation catheter or may include a plurality of needles. It is also understood that RF fluid source 14 and RF current generator 12 may be combined into a single operational structure controlled by an appropriate microprocessor for a controlled delivery of ablating fluid and a controlled application of RF current, both based upon measured parameters such as, but not limited to, flow rate, tissue temperature at the ablation site and at areas surrounding the ablation site, impedance, the rate of change of the impedance, the detection of arcing between the surgical instrument and the tissue, the time period during which the ablation procedure has been operating, and additional factors as desired.

It is also understood that while surgical instrument 16 is shown in FIG. 1 as including both the current delivery device and the fluid delivery device the present system is not so limited but could include separate needles or other instruments useful in RF liquid ablation procedures. For example, a single straight or coiled needle having an exposed end and a fluid flow path there through could be used to deliver both fluid and current to the target tissue for ablation purposes. Alternatively, a first needle could be used to deliver the current and a separate second needle or plurality of needles could be used to deliver fluid to the target tissue.

The application of the present system is not limited to the use of straight needles or helical needles as surgical instruments but could find use with any type of instrument wherein a conductive solution is delivered to a tissue and an RF current is applied to the tissue through the conductive fluid. Such instruments thus would include straight needles, helical needles, forceps, roller balls, instruments for the treatment of vascular disorders, and any other instrument.

System 10 can further include a second fluid delivery system including protective fluid source 18 and delivery instrument 19. The second fluid delivery system for delivery of tissue protecting fluid as described below via delivery instrument 19 for delivery of protective fluid to a tissue whose ablation is not desired.

At various times, a target tissue for a RF ablation procedure using a virtual electrode may be closely adjacent to tissue whose damage would be very undesirable. In general, it is typically desirable to limit the amount of damage due to the ablation procedure. With certain procedures, however, such as those involving the ablation of a metastases, it is critical that the ablation zone include at a minimum the entire metastases with some measurable portion of surrounding healthy tissue.

A method for protecting tissue surrounding a desired ablation zone will now be described. First, the appropriate RF ablating fluid delivery system and electrical electrode will be provided to the tissue to be ablated, such as RF current 12, RF ablating fluid source 14, and surgical instrument 16 previously described with reference to FIG. 1. Secondly, fluid delivery systems will be placed in, or over in the case of some surface ablations, the tissue to be protected to enable the treating physician to deliver to the tissue to be protected a tissue protecting fluid, such as protective fluid source 18 and delivery instrument 19 previously described with reference to FIG. 1. The tissue protecting fluid of protective fluid source 18 could comprise a nonconductive solution such as a sugar solution comprising water and dextrose or sucrose buffered to the appropriate pH. Alternatively, the tissue protecting fluid could comprise a chilled saline solution or other chilled biocompatible fluid that would act as a heat sink and limit the amount of heat absorbed by conduction from the tissue being ablated. It is understood that the tissue protecting fluid of protective fluid source 18 can be delivered via instruments of various types including but not limited to, needles of various configurations as previously described with reference to FIG. 1 where the interstitial provision of the tissue protecting fluid is desired, or some form of surface application device such as a roller ball or forceps where protection is desired along a tissue surface.

While a solution of sucrose or dextrose in water has been proposed as an example of a nonconductive solution useful with this invention, other biocompatible nonconductive solutions, including but not limited to other sugar solutions, glycols, and inositols could be used in accord with the present invention.

Figure 2:
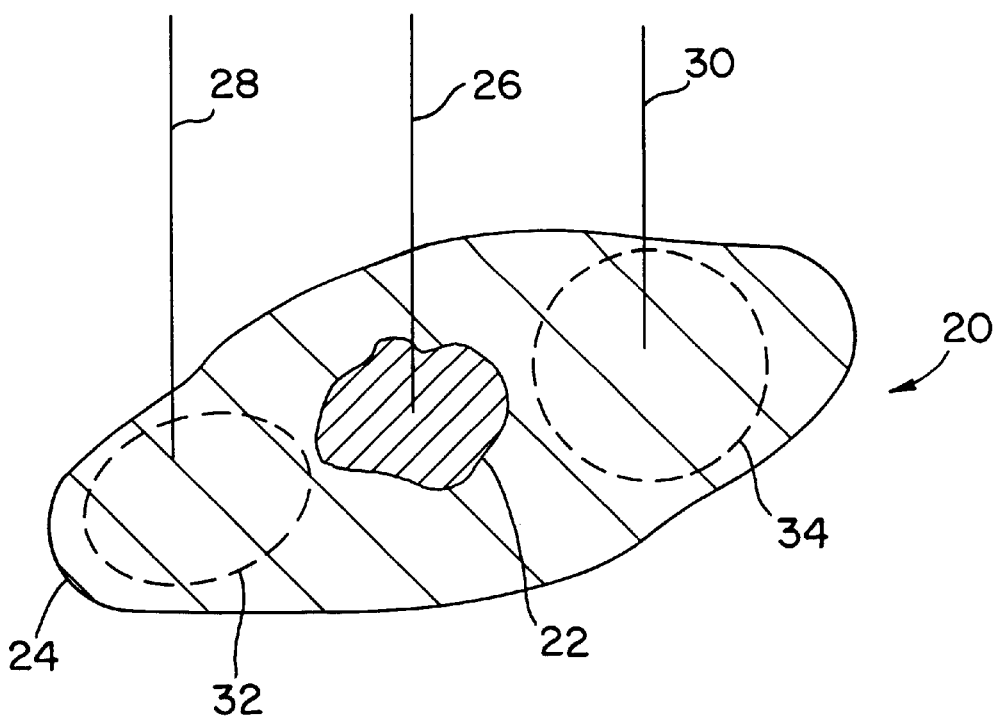
FIG. 2 is a perspective view of healthy tissue having tumorous tissue therein.

FIG. 2 is a perspective view of healthy tissue having tumorous tissue therein. As shown in FIG. 2, tissue 20 includes tumor 22 (or other tissue whose ablation is desired) and healthy tissue 24. Needle 26 is shown through which an RF conductive fluid, including but not limited to isotonic or hypertonic saline, and an RF current can be delivered to tumor 22. Also shown in FIG. 2 are needles 28 and 30 which represent delivery instrument 19 of FIG. 1 and which deliver tissue protecting fluid of protective fluid source 18 to the healthy tissue 24. Thus, boluses of protective nonconductive or cooled fluid within the healthy tissue are created, as indicated by dashed lines 32 and 34 respectively. It will be understood that FIG. 2 is highly schematic and is intended to illustrate the principle of the present invention and not the shape of any particular tissue or fluid bolus created within the tissue. Furthermore, it will be understood that needles 26, 28, and 30 are meant to be representative of various surgical instruments previously discussed in this application. Thus, instrument 26 could be a surface application device, including but not limited to a forceps.

The present invention has been described relative to the use of a bolus, which is commonly known in the medical profession as a specific volume of fluid that is static; that is, that is injected once. More commonly, the foregoing procedures are carried out with continuous infusion of the conductive solution.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. A method for the ablation of tissue and for the selected protection of tissue during an ablation therapy, the method comprising:
    delivering a conductive fluid to a target tissue site;
    penetrating a surface of a neighboring tissue site, wherein the neighboring tissue site is adjacent the target tissue site and ablation of the neighboring tissue site is not desired;
    infusing a protective fluid into tissue of the neighboring tissue site through the surface; and
    applying an electrical current to the delivered conductive fluid to ablate tissue of the target tissue site;
    wherein the protective fluid reduces ablation of the neighboring tissue site.

2. The method of claim 1, wherein delivering a conductive fluid includes:
    infusing the conductive fluid into the target tissue site.

3. The method of claim 1, wherein delivering a conductive fluid includes:
    providing the conductive fluid to the surface of the target tissue site.

4. The method of claim 1, wherein applying an electrical current to the delivered conductive fluid renders the delivered conductive fluid capable of ablating tissue.

5. The method of claim 1, further comprising:
    positioning an electrode to apply the electrical current to the conductive fluid.

6. The method of claim 5, wherein positioning the electrode includes contacting the delivered conductive fluid.

7. The method of claim 5, wherein positioning the electrode includes laterally spacing the electrode from the infused protective fluid.

8. The method of claim 5, wherein the electrode is positioned on a surface of the target tissue site to apply electrical current to the delivered conductive fluid.

9. The method of claim 5, wherein the electrode is positioned within the target tissue site to apply electrical current to the delivered conductive fluid.

10. The method of claim 5, wherein the neighboring tissue site has a front, a back, and a perimeter, and the electrode is laterally offset from the perimeter of the neighboring tissue site infused with the protective fluid.

11. The method of claim 5, wherein the target tissue site is defined by a front, a back, and a perimeter, and the neighboring tissue site is laterally offset from the perimeter of the target tissue site.

12. The method of claim 11, wherein the electrode is not aligned with the neighboring tissue site during the step of applying an electrical current.

13. The method of claim 12, wherein the electrode is aligned with the front of the target tissue site during the step of applying an electrical current.

14. The method of claim 1, wherein the step of infusing a protective fluid further comprises:
    providing a sugar solution consisting of water and dextrose to the neighboring tissue site.

15. The method of claim 1, wherein the step of infusing a protective fluid further comprises:
    providing a sugar solution consisting of water and sucrose to the neighboring tissue site.

16. The method of claim 1, wherein the step of infusing a protective fluid further comprises:
    providing a biocompatible non-conductive solution to the neighboring tissue site.

17. The method of claim 1, wherein the steps of delivering a conductive fluid and applying electrical current further comprises:
    providing the conductive fluid and the electrical current via a single needle.

18. The method of claim 1, wherein the steps of delivering a conductive fluid and applying electrical current further comprises:
    providing the conductive fluid and the electrical current via a plurality of needles.

19. The method of claim 1, wherein the step of infusing a protective fluid further comprises:
    providing a protective fluid to the neighboring tissue site via a single needle.

20. The method of claim 1, wherein the step of infusing a protective fluid further comprises:
    providing a protective fluid to the neighboring tissue site via a plurality of needles.

21. The method of claim 1, wherein the step of infusing a protective fluid includes:
    surrounding the target tissue site with protective fluid.

22. The method of claim 1, wherein the step of infusing a protective fluid includes:
    creating a plurality of protective fluid boluses about the target tissue site.

23. The method of claim 1, wherein the step of infusing a protective fluid includes:
    providing a chilled, electrically non-conductive fluid to the neighboring tissue site.

24. The method of claim 1, wherein the target tissue site is a tumor, and further wherein delivering a conductive fluid includes:

injecting the conductive fluid into the tumor.

25. The method of claim 24, wherein the neighboring tissue site is healthy tissue about the tumor.

26. The method of claim 1, wherein infusing a protective fluid includes reducing a conductivity of the neighboring tissue site.

* * * * *